United States Patent
Lucci et al.

(10) Patent No.: US 9,789,273 B2
(45) Date of Patent: Oct. 17, 2017

(54) SENSOR AND VALVE INTEGRATED INTO A PATIENT INTERFACE

(75) Inventors: Christopher Scott Lucci, Murrysville, PA (US); Harol Allen Lockhart, Mt. Pleasant, PA (US); David W. Smith, IV, Oakmont, PA (US); Nathan Francis O'Connor, Monroeville, PA (US); Jonathan Sayer Grashow, Cheswick, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 482 days.

(21) Appl. No.: 14/115,932

(22) PCT Filed: May 11, 2012

(86) PCT No.: PCT/IB2012/052361
§ 371 (c)(1),
(2), (4) Date: Nov. 6, 2013

(87) PCT Pub. No.: WO2012/156885
PCT Pub. Date: Nov. 22, 2012

(65) Prior Publication Data
US 2014/0069429 A1 Mar. 13, 2014

Related U.S. Application Data

(60) Provisional application No. 61/485,789, filed on May 13, 2011.

(51) Int. Cl.
*A61M 16/20* (2006.01)
*A61M 16/06* (2006.01)
(Continued)

(52) U.S. Cl.
CPC ........ *A61M 16/20* (2013.01); *A61M 16/0051* (2013.01); *A61M 16/06* (2013.01);
(Continued)

(58) Field of Classification Search
CPC .. A61M 16/06; A61M 16/0683; A61M 16/20; A61M 16/203; A61M 2016/0027;
(Continued)

(56) References Cited

U.S. PATENT DOCUMENTS

2005/0085799 A1 4/2005 Luria
2007/0163588 A1 7/2007 Hebrank
(Continued)

FOREIGN PATENT DOCUMENTS

CN 101495170 A 7/2009
CN 101502690 A 8/2009
(Continued)

*Primary Examiner* — Peter S Vasat
(74) *Attorney, Agent, or Firm* — Michael W. Haas

(57) ABSTRACT

An improved patient interface assembly and pressure support system integrate a pressure sensor and a valve into the patient interface assembly and employs closed loop control between the sensor and the valve in order to limit delay between the time at which a condition indicative of abnormal breathing or flow load during normal breathing is experienced by a patient and the time at which altered pressure support is received by the patient.

14 Claims, 8 Drawing Sheets

(51) Int. Cl.
*A61M 16/00* (2006.01)
*A61M 16/08* (2006.01)

(52) U.S. Cl.
CPC ....... *A61M 16/203* (2014.02); *A61M 16/0683* (2013.01); *A61M 16/0825* (2014.02); *A61M 2016/0027* (2013.01); *A61M 2205/3331* (2013.01); *A61M 2205/3561* (2013.01); *A61M 2205/3592* (2013.01)

(58) Field of Classification Search
CPC .. A61M 2205/3331; A61M 2205/3561; A61M 2205/3592
See application file for complete search history.

(56) References Cited

U.S. PATENT DOCUMENTS

| | | |
|---|---|---|
| 2007/0193579 A1 | 8/2007 | Duquette |
| 2008/0251079 A1 | 10/2008 | Richey |
| 2010/0252037 A1 | 10/2010 | Wondka |
| 2011/0011400 A1* | 1/2011 | Gentner ................ A61M 16/00 128/204.18 |
| 2016/0303338 A1 | 10/2016 | Kenyon |

FOREIGN PATENT DOCUMENTS

| | | |
|---|---|---|
| EP | 0798005 A2 | 10/1997 |
| WO | WO2006053124 A2 | 5/2006 |

* cited by examiner

SENSOR AND VALVE INTEGRATED INTO A PATIENT INTERFACE

CROSS-REFERENCE TO RELATED APPLICATIONS

This patent application claims the priority benefit under 35 U.S.C. §371 of international patent application no. PCT/IB2012/052361, filed May 11, 2012, which claims the priority benefit under 35 U.S. C. §119(e) of U.S. Provisional Application No. 61/485,789 filed on May 13, 2011, the content of which are herein incorporated by reference.

BACKGROUND OF THE INVENTION

1. Field of the Invention

The present invention relates to airway pressure support systems and, more particularly, to a patient interface assembly for a pressure support system in which a pressure sensor and a valve of a flow control circuit are integrated into the patient interface assembly.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

Devices are known that attempt to detect apneas and hypopneas to determine in real time whether a patient suffers from a sleep apnea syndrome. Examples of conventional apnea/hypopnea detection devices are described in U.S. Pat. No. 5,295,490 to Dodakian; U.S. Pat. No. 5,605,151 to Lynn; U.S. Pat. No. 5,797,852 to Karakasoglu et al.; U.S. Pat. No. 5,961,447 to Raviv et al.; U.S. Pat. No. 6,142,950 to Allen et al.; U.S. Pat. No. 6,165,133 to Rapoport et al.; U.S. Pat. No. 6,368,287 to Hadas.

It is further well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP).

It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing. Thus, the effectiveness of treating a patient via an auto-titration type of pressure support system can depend to a great extent on the accurate detection of apneas and/or hypopneas.

Examples of conventional auto-titration pressure support system are disclosed in U.S. Pat. No. 5,245,995 to Sullivan et al.; U.S. Pat. Nos. 5,259,373; 5,549,106, and 5,845,636 all to Gruenke et al.; U.S. Pat. Nos. 5,458,137 and 6,058,747 both to Axe et al.; U.S. Pat. Nos. 5,704,345; 6,029,665, and 6,138,675 all to Berthon-Jones; U.S. Pat. No. 5,645,053 to Remmers et al.; and U.S. Pat. Nos. 5,335,654; 5,490,502, 5,535,739, and 5,803,066 all to Rapoport et al. All of these conventional pressure support systems, with the possible exception of U.S. Pat. No. 5,645,053 to Remmers et al., are reactive to the patient's monitored condition. That is, once a condition occurs that indicates abnormal breathing, the system alters the pressure support to treat this condition.

It is also known, however, that known pressure support systems have certain shortcomings associated with delays in the detection of breathing conditions and additional delays in therapeutically altering the pressure support in response to the breathing conditions. A pressure source such as a CPAP machine is typically connected with a patient interface device through the use of a long flexible tube that carries the flow of fluid such as breathing gases from the pressure source to the patient interface device. Such supply tubes typically have been 22 millimeters in diameter and six feet in length. A pressure variation within air typically moves at a speed of approximately one foot per millisecond and thus takes roughly six milliseconds to traverse a six foot length of tubing. When a patient experiences a condition that is indicative of abnormal breathing, the pressure variation that results from the condition takes roughly six milliseconds to be communicated from the patient interface through the six feet of tubing in order to be detected by a sensor situated on the pressure source (a pressure variation can also occur under normal breathing due to flow load changes). While the pressure source may be capable of altering its pressure very rapidly, the altered pressure likewise takes six milliseconds to travel from the pressure source and along the six foot length of tubing to be received at the patient interface. The total delay between the onset of the condition at the patient and the receipt by the patient of altered pressure support can thus be roughly twelve milliseconds. This delay is further increased by the system dynamics of the mechanism used to adjust the pressure.

In today's systems, the time delay just described is managed via control algorithms that assume a constant and consistent level of airflow resistance and (volumetric) compliance. This assumption in the algorithms severely limits airflow circuit designs to standard structures with relatively large cross sectional areas that provide generally constant and consistent levels of airflow resistance and compliance. The result is that masks are typically equipped with a relatively large and inflexible elbow near the nose, which is then connected to a relatively large and inflexible hose. For example, in a typical standard mask and elbow connected to a six foot hose, the total resistance at 60 LPM flow rate is $5\times10^{-3}$ LPM/cm H2O (the hose)+$16.7\times10^{-3}$ LPM/cm H2O (the mask and elbow)=$21.7\times10^{-3}$ LPM/cm H2O. In addition, this resistance will typically vary by only about $1.5\times 10^{-3}$ LPM/cm H2O.

It is desirable, however, to be able to employ improved mask designs that may be defined by small and flexible tubing combined with unconventional airflow paths instead of the standard structures above. These features, however, will (by definition) have high resistance to airflow, and the resistance levels could change significantly throughout the course of the night (i.e. they are not constant and consistent). In addition, soft materials could have relatively high mechanical deformation which would lead to significant and variable volumetric compliance in the airflow circuit. There is thus a need for a solution that permits the use of such improved mask designs.

SUMMARY OF THE INVENTION

Accordingly, an improved patient interface assembly and pressure support system integrate a pressure sensor and a valve into the patient interface assembly and employs closed loop control between the sensor and the valve. This configuration reduces the time delay between the time at which a condition indicative of abnormal breathing or flow load during normal breathing is experienced by a patient and the time at which altered pressure support is received by the patient, and, as a result, empowers compensation for compliance and resistance variability in the air flow circuit and thus allows for use of improved mask designs as described above.

Accordingly, an aspect of the present invention is to provide an improved pressure support system and patient interface assembly that provide improved therapeutic patient monitoring.

Another aspect of the present invention is to provide an improved pressure support system and patient interface assembly that provide improved therapeutic pressure support to the patient.

Another aspect of the present invention is to provide an improved patient interface assembly having a pressure sensor and a valve integrated therein.

Another aspect of the present invention is to provide an improved patient interface assembly and pressure support system that enable improved control of pressure support provided to a patient.

Another aspect of the present invention is to provide an improved patient interface assembly and pressure support system that overcome known shortcomings of known pressure support systems.

In one embodiment, a patient interface assembly structured to be in fluid communication with a pressure source that provides a flow of a fluid is provided that includes a patient interface device having a chamber formed therein that is structured to be in fluid communication with a breathing passage of a patient, the patient interface device being structured to be positioned on a head of the patient when the patient interface assembly is donned by the patient, a first pressure sensor structured to detect pressure conditions within the chamber, the first pressure sensor being structured to be positioned on the head of the patient when the patient interface assembly is donned by the patient, a valve structured to be positioned on the head of the patient when the patient interface assembly is donned by the patient, and a compliant tube element having variable compliance and resistance properties and being structured to be positioned on the head of the patient when the patient interface assembly is donned by the patient, the patient interface device being positioned downstream of the valve through the tube element. Closed loop control is employed to control the valve and thereby the pressure delivered to the patient through the patient interface device based on at least the pressure conditions detected by the first pressure sensor.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1:
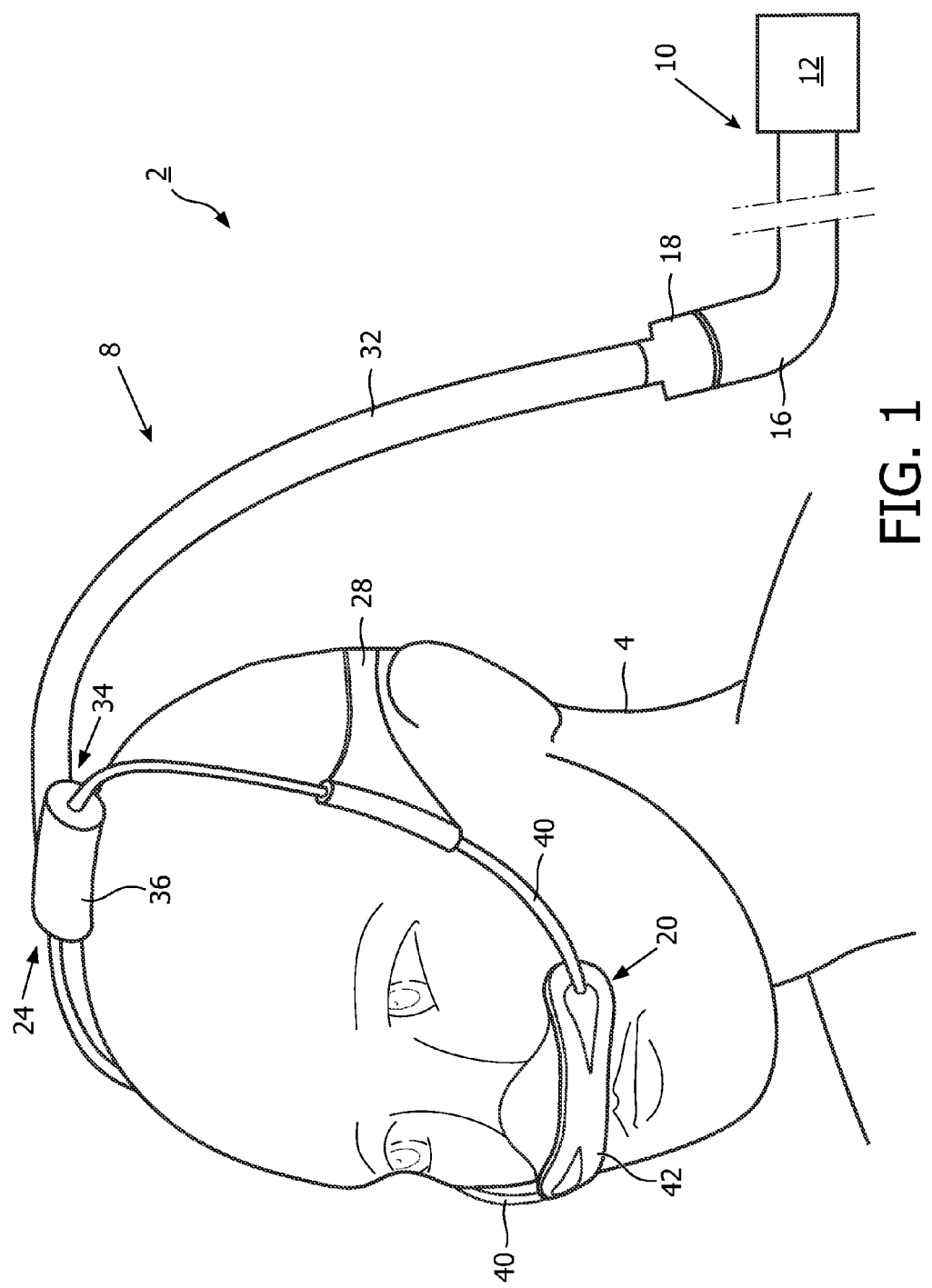
FIG. 1 is a view of a pressure support system according to one particular, non-limiting embodiment in which the present invention in its various embodiments may be implemented.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein An improved pressure support system 2 is depicted in FIG. 1 a portion of which is situated on a patient 4. Pressure support system 2 is also depicted schematically in FIG. 2. Improved pressure support system 2 can be stated as including an improved patient interface assembly 8 and a pressure source 10 in fluid communication with one another.

In the exemplary embodiment depicted herein, pressure source 10 is a device that generates a flow of gas, such as a CPAP machine 12, from which extends an elongated supply tube 16, also known as a patient circuit, at the free end of which is situated a swivel reducer 18. The supply tube 16 may be, for instance and without limitation, a flexible 22 mm diameter tube that is six feet in length. Swivel reducer 18 has a relatively wider first end connected with the free end of supply tube 16 and has a relatively narrower second end that can be connected with patient interface assembly 8. The narrow end of swivel reducer 18 enables connection of a 15 mm diameter tube, by way of example and without limitation, and further provides a swivel feature that enable supply tube 16 and patient interface assembly 8 to rotate with respect to one another. It is noted that the exemplary supply tube 16 and swivel reducer 18 are optional structures that are not intended to be in any fashion limiting. Pressure source 10 is configured to provide a flow of pressurized fluid, such as air or other breathing gases, to patient interface assembly 8 for breathing by patient 4.

Figure 3:
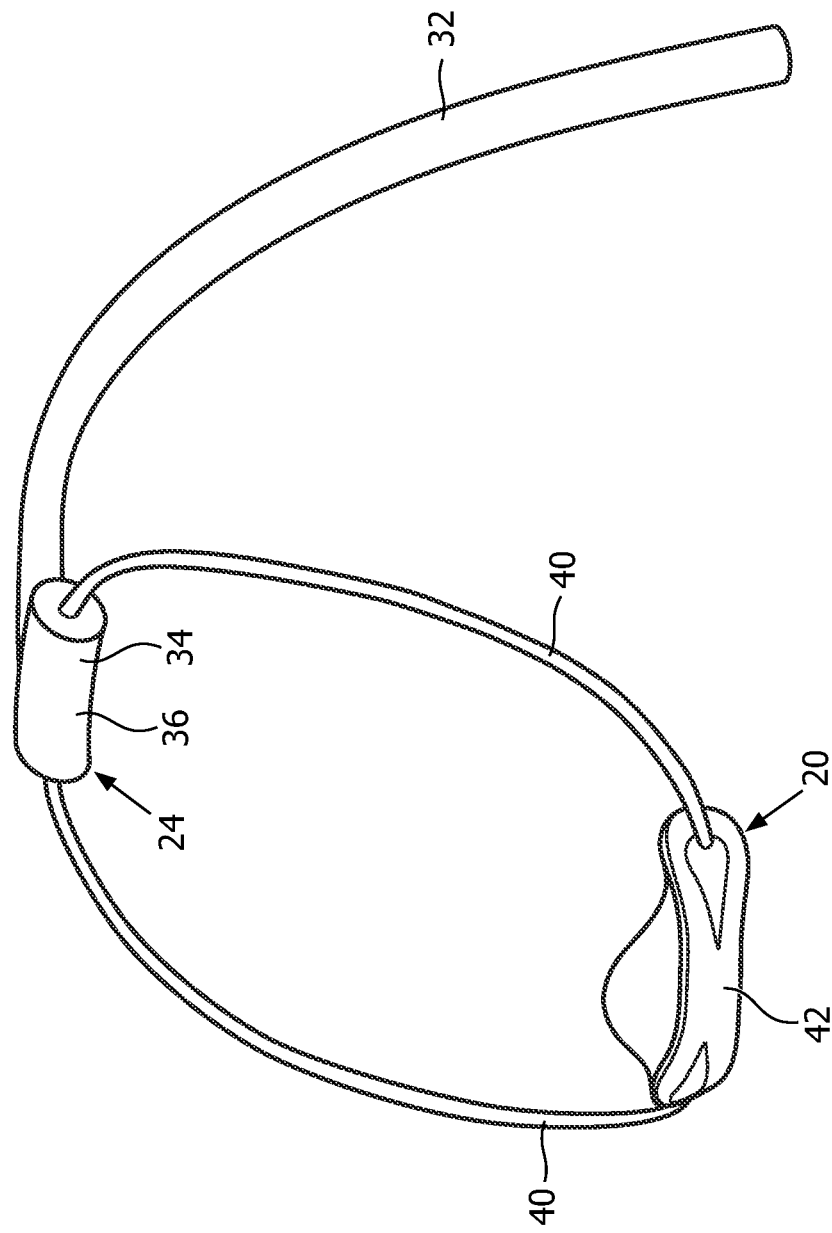
FIG. 3 is view of a portion of a patient interface assembly of the pressure support system of FIG. 1.

Patient interface assembly 8 can be said to include a patient interface 20, a fluid connection apparatus 24, a flow control circuit 26, and a headgear 28. It is noted that patient interface assembly 8 is depicted in FIG. 3 without patient 4 and without headgear 28 for purposes of simplicity and clarity. It is expressly noted that patient interface assembly 8 as described herein is merely one example of many patient interface assembly that can be configured in the fashion set forth below to achieve the desirable results of the present invention. The description of patient interface assembly 8 is thus not intended to be limiting in any fashion whatsoever.

Fluid connection apparatus 24 can be said to include a flexible attachment tube 32 that can be connected with swivel reducer 18 and which is, in the depicted exemplary embodiment, a piece of 15 mm diameter tubing. Fluid connection apparatus 24 can further be said to include a manifold apparatus 34 having a housing 36 and as further including a pair of highly compliant, flexible fluid connection elements 40 that extend between manifold apparatus 34 and patient interface 20. Fluid connection elements 40 are lengths of narrow diameter flexible tubing that enable fluid communication between manifold apparatus 34 and patient interface 20. In the depicted exemplary embodiment the connection elements 40 flow in a parallel relationship in order to enable uninterrupted flow if patient 4 sleeps on his or her side and partially or fully blocks one of the connection elements 40. As can be understood from FIG. 1, the exemplary headgear 28 is mounted to fluid connection elements 40 and extends behind the head of patient 4, although headgear 28 could be of any of a wide variety of different configurations without departing from the present concept.

Patient interface 20 includes a housing 42 having a chamber 44 (FIG. 2) formed therein that is in fluid communication with fluid connection elements 40. Patient interface 20 additionally includes a cushion 48 that is disposed on housing 42 and that is configured to directly contact patient 4 and to provide a seal between chamber 44 and the outside atmosphere. An exhaust port 50 is depicted in FIG. 2 as being formed in housing 42, but it is understood that exhaust port 50, which provides an opening for expiratory air flow, can be provided elsewhere on the patient interface assembly 8 or potentially on the pressure source 10 without departing from the present concept.

Figure 2:
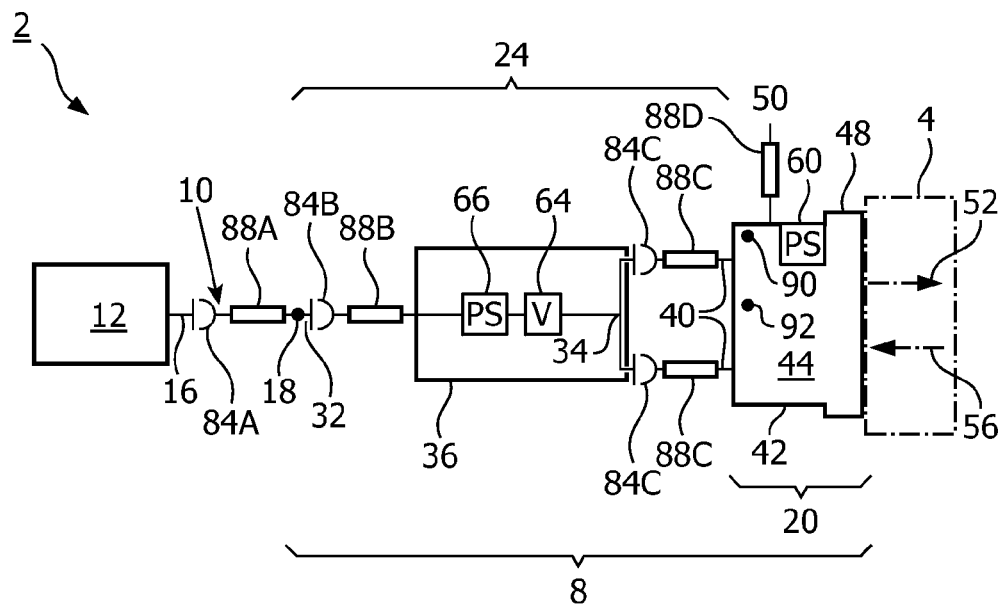
FIG. 2 is a schematic depiction of the pressure support system of FIG. 1.

FIG. 2 schematically depicts an inspiratory air flow at an arrow 52 and further depicts an expiratory air flow at an arrow 56. The arrows 52 and 56 are intended to be representative of a breathing passage of patient 4 and to demonstrate that the various components of pressure support system 2 are in fluid communication with the breathing passage of patient 4.

Figure 4A:
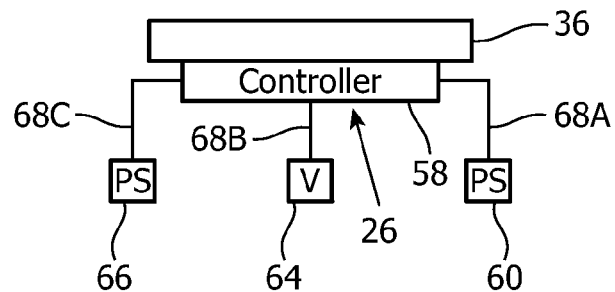
FIG. 4a is a schematic depiction of a flow control circuit of the patient interface assembly of FIG. 3.

As can be understood from FIGS. 2 and 4a, flow control circuit 26 is a closed loop control system that includes a controller 58 which, in the exemplary embodiment depicted in FIG. 4a, is disposed on housing 36 of manifold apparatus 34 but which, as is stated in greater detail elsewhere herein, can be situated elsewhere on pressure support system 2. Flow control circuit 26 further includes a pressure sensor 60 and a valve 64. In the exemplary embodiment of flow control circuit 26 depicted herein, an additional pressure sensor 66 is provided, although it is noted that pressure sensor 66 is optional. Pressure sensor 60, valve 64, and pressure sensor 66 are in electronic communication with controller 58 through the use of a number of wires 68A, 68B, and 68C. Of course, wireless communication between the various elements is also contemplated by the present invention.

Pressure sensor 66 can be said to be situated upstream of valve 64, meaning that it is situated between valve 64 and CPAP machine 12. Pressure sensor 60 can be said to be downstream of valve 64 because it is situated on an opposite side of valve 64 from pressure sensor 66 and is situated downstream of CPAP machine 12 and the flow of fluid provided therefrom.

Advantageously, pressure sensor 60 is situated on housing 42 and in fluid communication with chamber 44 in order to detect a pressure condition within chamber 44, which enables detection of an abnormal breathing condition in patient 4. By situating pressure sensor 60 in a position whereby it directly detects pressure conditions within chamber 44, the abnormal breathing condition experienced by patient 4 can be detected extremely rapidly since the distance between pressure sensor 60 and the breathing passage of patient 4 is extremely small. In so doing, pressure sensor 60 generates a signal that is detected by controller 58 as an input signal that is representative of a pressure within chamber 44.

Controller 58 has a microprocessor and a memory, with the memory having stored therein one or more routines which are executable on the microprocessor. The routines can be in any of a variety of forms and can perform any of a variety of functions that enable the control of pressurized fluid provided to patient 4. In the exemplary embodiment depicted herein, the routines executable on controller 58 include one or more of proportional, integral, and derivative control functions, and the controller 58 thus functions as a PID controller in the exemplary embodiment depicted herein, as well as providing other functions. Other embodiments could include some combination of proportional controller with phase lag (integral is a specific type of phase lag) or phase lead (derivative is a specific type of phase lead) as well as feedforward terms. Additionally, this could include additional control techniques such as state-space control, robust $H_\infty$ control, etc.

In response to the input signal from pressure sensor 60, controller 58 generates an output signal that is communicated to valve 64 to adjust the position of a movable valve element and to thereby adjust the pressure of the fluid that is provided downstream of valve 64. In this regard, pressure sensor 66 that is situated upstream of valve 64 also provides an input signal to controller 58 in order to enable controller 58 to more accurately generate the desired position of the valve element of valve 64 as represented by the output signal provided from controller 58 to valve 64.

It is noted that the desired position of the movable valve element of valve 64 can be determined by controller 58 based upon pressure conditions existing upstream and downstream of valve 64 as determined by pressure sensor 60 and pressure sensor 66 and as communicated to controller 58, which is to say that the desired final position of the movable valve element of valve 64 can be determined based upon pressure conditions in existence at the time an adjustment of valve 64 is determined to be necessary rather than by incrementally moving the movable valve element over a period of time with further signals from pressure sensor 60 and pressure sensor 66 being relied upon to determine the correct setting of valve 64.

In other words, the provision of pressure sensor 60 and pressure sensor 66 enables accurate initial positioning of the movable element of valve 64, and further signals from pressure sensor 60 and pressure sensor 66 are employed by controller 58 for fine tuning of the setting of valve 64. Signals from pressure sensor 60 and pressure sensor 66 are thus used to enable accurate initial setting of valve 64 by controller 58 rather than being relied upon for positioning of the movable valve element through a series of incremental adjustments of valve 64 until desirable pressure conditions in chamber 44 are achieved. It is noted, however, that the signals from pressure sensor 60 and pressure sensor 66 can be employed in numerous fashions in the control of valve 64.

As can be understood from FIG. 2, valve 64 and pressure sensor 66 are disposed on manifold apparatus 34 within the interior of housing 36 in a first embodiment of the present invention. FIG. 2 depicts valve 64 and pressure sensor 66 as being spaced apart from one another, but it is understood that such spacing is depicted merely for purposes of clarity and simplicity, and it is understood that valve 64 and pressure sensor 66 may be disposed very close to one another, although on the other hand they may be spaced apart from one another without departing from the present concept.

By situating valve 64 on manifold apparatus 34, which is in relatively close proximity to patient interface 20, pressure adjustments made by valve 64 that are instructed by controller 58 are communicated relatively rapidly to patient interface 20 and to patient 4. In view of the size of the typical human head, valve 64 will typically be situated a distance of less than one foot from the breathing passage of patient 4, with the result that changes in pressure of the fluid that result from action of valve 64 are communicated to patient 4 with a delay of well under one millisecond, which is very advantageous.

Because pressure sensor 60 is situated in very close proximity to the breathing passage of patient 4, and because valve 64 is (in the depicted exemplary first embodiment) situated a distance of less than one foot from the breathing passage, the overall delay between the detection of a condition that indicates abnormal breathing or flow load during normal breathing in patient 4 and the resultant alteration of system pressure by valve 64 still has an overall delay of less than one millisecond, which is highly advantageous. Providing such a relatively small delay between the occurrence of a condition and the provision of therapeutic pressure to alleviate the condition is beneficial since it rapidly provides therapeutic air pressure to patient 4 with minimal delay.

Moreover, the degree of control over air pressure that is afforded by flow control circuit 26 is also highly advantageous. By situating pressure sensor 60 and valve 64 to largely eliminate delays between the onset of a condition and the provision of pressure therapy to alleviate the condition enables the use of more rapidly responding valves and valve commands. Regarding valve commands, it is understood that in a system in which a 12 millisecond delay is inherent, valve control signals will be configured to make relatively small changes to a valve in order to avoid instability of the control system or other undesirable effects such as overshoot. However, in a system such as is described herein in which the delay between an onset of a condition and the provision of therapeutic relief is minimal (e.g., less than one millisecond), output signals to adjust the position of valve 64 can be made much more aggressively in order to provide a more rapid change in fluid pressure since the corresponding change in fluid pressure will be detected with only an extremely small delay, which provides for improved control of pressure.

It is understood that a valve can be considered to have a "gain", which refers to a differential equation that is associated with valve 64 and that characterizes the incremental change in pressure that will result from an incremental change in position of the movable valve element given the pressure conditions on both sides of valve 64. Gain can be linear or nonlinear with change in position of the movable valve element. Also, gain can be relatively high, meaning that a small change in valve position results in a large change in pressure, or can be relatively low, meaning that a small change in valve position results in a small change in pressure. Control systems with a relatively large time lag between a change in state and a detection of a result typically have needed to have relatively low overall system gains (e.g., using either or both of valves having a relatively low gain or a low controller gain) in order to avoid instability in the control system. However, with a control system which has minimal delay, such as in the system described herein, higher overall system gains (e.g., using either or both of valves having a relatively high gain or a high controller gain) can be employed to enable more aggressive pressure change commands to be carried out successfully due to the rapid detection of pressure by pressure sensor 60 with minimal delay.

It thus can be seen that whereas previous systems had a relatively large twelve millisecond delay due to the delay inherent in the transport of a fluid and the positioning of the valve and sensor six feet or more away from the patient, patient interface assembly 8 and pressure support system 2 advantageously alleviate such issues by providing pressure sensor 60 and valve 64 in relatively close proximity to the breathing passage of patient 4. It is understood, however, that variations from the foregoing can be implemented without departing from the present concept. For instance, controller 58 is depicted as being situated on fluid connection apparatus 24. It is understood that in other embodiments, controller 58 could be integrated into patient interface 20 in whole or in part without departing from the present concept.

Figure 4B:
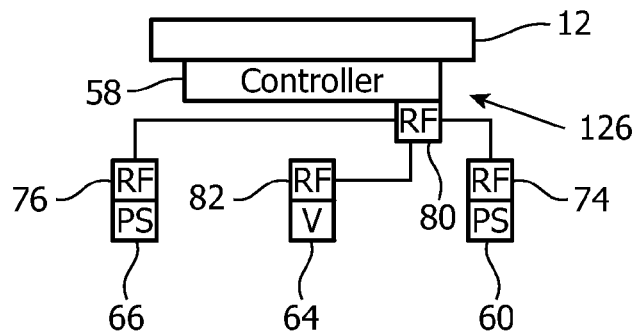
FIG. 4b is an alternate schematic depiction of a flow control circuit of the patient interface assembly of FIG. 3.

Still alternatively, and as is depicted generally in FIG. 4b, an alternate flow control circuit 126 can employ a wireless communication apparatus 72 instead of wires 68A, 68B, and 68C, and controller 58 can be situated on CPAP machine 12. Wireless communication apparatus 72 would provide wireless communication between controller 58 and pressure sensors 60 and 6 and valve 64 using radio frequency transmitters, infrared transmitters, Bluetooth communication, etc. without limitation. In the embodiment depicted generally in FIG. 4b, wireless communication apparatus 72 includes a pair of RF transmitters 74 and 76 that are situated for use with pressure sensors 60 and 66, respectively. Wireless communication apparatus 72 further includes a pair of RF transceivers 80 and 82 that cooperate with controller 58 and valve 64, respectively. RF transmitters 74 and 76 transmit to RF transceiver 80 and thus to controller 58 wireless signals that are representative of pressure values detected by pressure sensors 60 and 66. RF transceiver 80 then transmits to RF transceiver 82, and thus to valve 64, a wireless signal representative of a movement of the movable valve element of valve 64 to effect a change in pressure of the fluid in patient interface 20.

In the embodiment depicted herein, valve 64 cooperates with RF transceiver 82 rather than merely cooperating with an RF receiver since valve 64 additionally is configured to provide to controller 58 a signal representative of the physical position of the movable element of valve 64. Such a signal representative of the physical position of the movable valve element can also be provided with wire 68B as is depicted generally in FIG. 4a. By providing the physical position of valve 64 to controller 58, the control system and its commands can be made even more aggressively and accurately because of the aforementioned known transport function associated with valve 64. That is, the change in pressure that will result from a certain change in position of the movable valve element of valve 64 is characterized in the transport function which is stored in the form of a routine on controller 58.

By knowing the current position of the movable element of valve 64, by knowing the pressures on either side of valve 64 through the use of pressure sensors 60 and 66, and by detecting a condition in the patient with the use of pressure sensor 60, controller 58 can provide to valve 64 an instruction that can be characterized as an instruction to move from a first point to a second point. Such a control instruction is more accurate and more aggressive than a movement command which will rely upon further detections of pressures in order to adjust the valve setting from an initial gross setting to a final desired setting.

It is noted that the flexible tubing depicted in FIG. 2 is also schematically depicted as having a compliance property, as indicated at the electronic capacitor symbols with the numerals 84A, 84B, and 84C, and further includes a resistance property represented by the electronic resistor symbols and indicated at the numerals 88A, 88B, and 88C. For instance, supply tube 16 includes both a compliance property 84A and a resistance property 88A. A "compliance" property refers to a volume change with increased pressure, such as in the way a partially deflated section of flexible tubing will become slightly more expanded with inflation due to increased pressure, with such expansion resulting in a change in volume which represents fluid that is not an inspiratory air flow. A "resistance" refers to a resistance to fluid flow. Attachment tube 32 likewise includes a compliance property 84B and a resistance property 88B. Fluid connection elements each include a compliance property 84C and a resistance property 88C. Exhaust port 50 include a resistance property 88D.

The various compliance and resistance properties are illustrated in FIG. 2 in order to further demonstrate the advantages of positioning valve 64 and pressure sensor 66 relatively close to the breathing passage of patient 4. That is, controller 58 employs the aforementioned transport function that is associated with valve 64 in order to determine a position of the movable valve element of valve 64 in adjusting pressure within chamber 44. However, controller 58 also includes and employs routines which characterize the flow characteristics of manifold apparatus 34 and fluid connection elements 40 in controlling valve 64. In particular, the aforementioned fluid flow properties of fluid connection elements 40 are characterized by compliance property 84C and resistance property 88C. Notably, by retaining compliance properties 84A and 84B as well as resistance properties 88A and 88B of supply tube 16 and attachment tube 32 upstream of valve 64, their effects on flow control circuit 26 can be largely ignored since they are not disposed between valve 64 and pressure sensor 60. By minimizing the number of variables that can affect the pressure in chamber 44, i.e., by ignoring compliance properties 84A and 84B and resistance properties 88A and 88B, the pressure in chamber 44 can be more rapidly and accurately varied as needed.

In one embodiment, compliance property 84C may vary by as much as about ±60 ml at 20 cm H2O and resistance property 88C may vary by as much as about $\pm 100 \times 10^{-3}$ LPM/cm H2O at 60 LPM flow rate (in one particular embodiment it may vary by as much as about $\pm 33 \times 10^{-3}$ LPM/cm H2O at 60 LPM flow rate) with appropriate control and compensation therefore being provided by the closed loop control system implemented in flow control circuit 26 as described elsewhere herein. In addition, the total resistance of patient interface assembly 8 that may be overcome is only limited by the pressure generating capacity of the compressor of CPAP machine 12. In one exemplary embodiment, the total resistance of patient interface assembly 8 that may be overcome with the present invention is about 1500× $10^{-3}$ LPM/cm H2O or more at 60 LPM, with a total resistance variation of about ±100×$10^{-3}$ LPM/cm H2O or more, with appropriate control and compensation therefore being provided by the closed loop control system implemented in flow control circuit 26 as described elsewhere herein.

It thus can be understood that in alternate embodiments, pressure sensor 60, valve 64, and pressure sensor 66 can be in different positions. For instance, in the first exemplary embodiment depicted in FIG. 2, pressure sensor 60 is currently depicted as being situated generally between exhaust port 50 and the breathing passage of patient 4. However, pressure sensor 60 could be situated at the location indicated at the numeral 90 (FIG. 2). If pressure sensor 60 is relocated to location 90, resistance property 88D of exhaust port 50 will have a different effect on pressure sensor 60, which will have to be taken into account by controller 58 in controlling valve 64.

An alternate position of valve 64 is indicated in FIG. 2 at the numeral 92. In such a position, i.e., on patient interface 20, pressure sensor 60 and valve 64 would be in even closer proximity and could provide an even greater level of control of the pressure within chamber 44. Also, such positioning of valve 64 would avoid the need to consider compliance property 84C and resistance property 88C of fluid connection elements 40.

Pressure sensor 66 could alternatively be situated in swivel reducer 18. Such an alternative positioning would require controller 58 to take into account compliance property 84B and resistance property 88B of attachment tube 32 in controlling valve 64.

It thus is to be understood that the various positions of pressure sensor 60, valve 64, and pressure sensor 66 mentioned herein can be provided in any combination, and still other positioning of such elements is possible without departing from the present concept. Moreover, the positioning of controller 58 and the use of wireless communication apparatus 72 likewise can likewise be provided in any combination.

As described elsewhere herein, the present invention provides an improved patient interface assembly and pressure support system that integrate a pressure sensor and a valve into the patient interface assembly and employs closed loop control between the sensor and the valve. The following discussion describes a number of important considerations relating to closed loop control systems, particularly in connection with pressure support therapy such as PAP therapy, that may be relevant to designing a particular closed loop control methodology for use with the present invention.

Effective PAP therapy requires control of the pressure provided to the patient. The mechanism used to maintain for the desired output of a system is commonly referred to as a control system. A typical feedback control system comprises a process to be controlled (plant), a sensor (or estimator) to assess the state of the physical control parameter, and a controller that regulates the system. In this instance (PAP therapy), the pressure sensor (or estimate from surrogates) is the feedback mechanism for the pressure generator (plant) to maintain the desired therapy pressure. The output of the pressure sensor is "fed-back" to the controller to allow the controller to adjust for any residual differences between the actual pressure and the desired pressure. This difference is called the "error" term and results in control action causing the actual pressure to converge to the pressure setpoint.

There are two main stimuli that dominate the pressure error, setpoint changes (that is changes in the desired pressure) and load-side disturbances (in this case, flow changes from the patient or pneumatic system used to provide therapy.)

Figure 5:
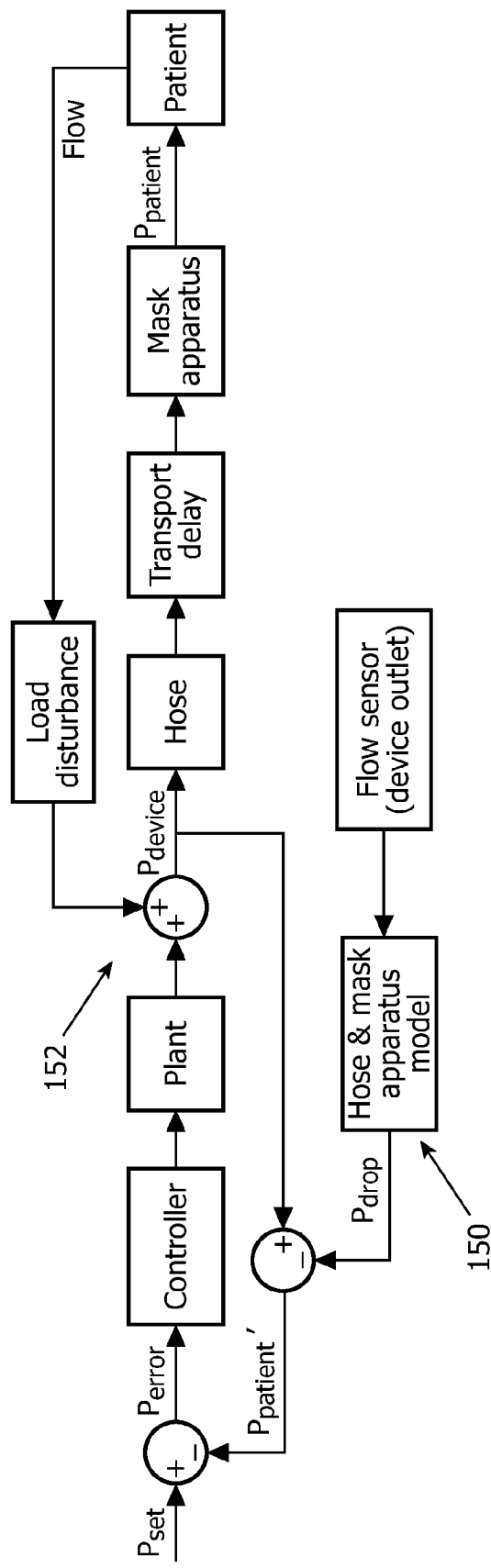
FIG. 5 is a block diagram of the closed-loop feedback system of the pressure loop of a prior art PAP device with the pressure loop closed around an estimate of the patient pressure.

FIG. 5 is a block diagram of the closed-loop feedback system 150 of the pressure loop of a prior art PAP device 152 with the pressure loop closed around an estimate of the patient pressure. The actual pressure from FIG. 5 is typically measured at the outlet of the device. Compensation is performed to account for any pressure drops that occur in the hose and patient interface assembly to yield an estimate of patient pressure. However, differences in hose length, diameter, and configuration (bends, etc.) in combination with different patient interface assembly result in different transfer functions (that is the functional relationship between input and output pressures) to characterize the difference between the outlet pressure and the patient pressure. Additional complications arise from closing the pressure feedback loop with patient pressure due to the transport delay in the system.

Figure 6:
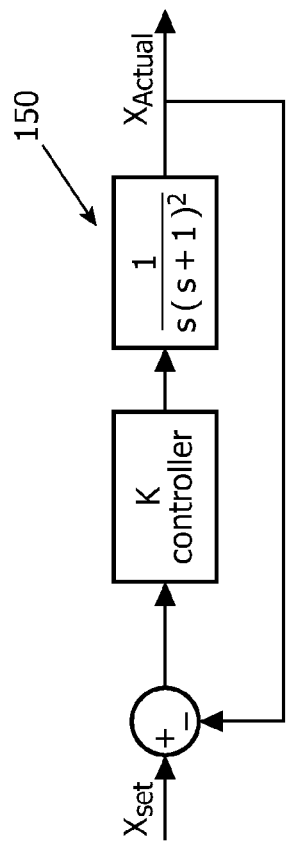
FIG. 6 is a block diagram of an exemplary arbitrary closed loop system used to demonstrate the effects of a time delay on system response and stability.

This delay can affect the relative stability of the system and system dynamics and response rate to any pressure error. For example, consider the arbitrary closed-loop system 154 as shown in FIG. 6. The plant of the system is $$G(s) = \frac{1}{s(s+1)^2}$$

in the Laplace domain, which is a commonly used transformation for analyzing linear-time invariant systems. In this illustration, the controller is a proportional only controller, indicating that the only control action applied is a gain to the error between the setpoint and actual value. The closed-loon transfer function of the unity feedback system is $$\frac{X_{Actual}}{X_{Set}} = \frac{KG(s)}{1 + KG(s)} = \frac{K}{s^2 + 2s^2 + s + K}.$$

Figure 7:
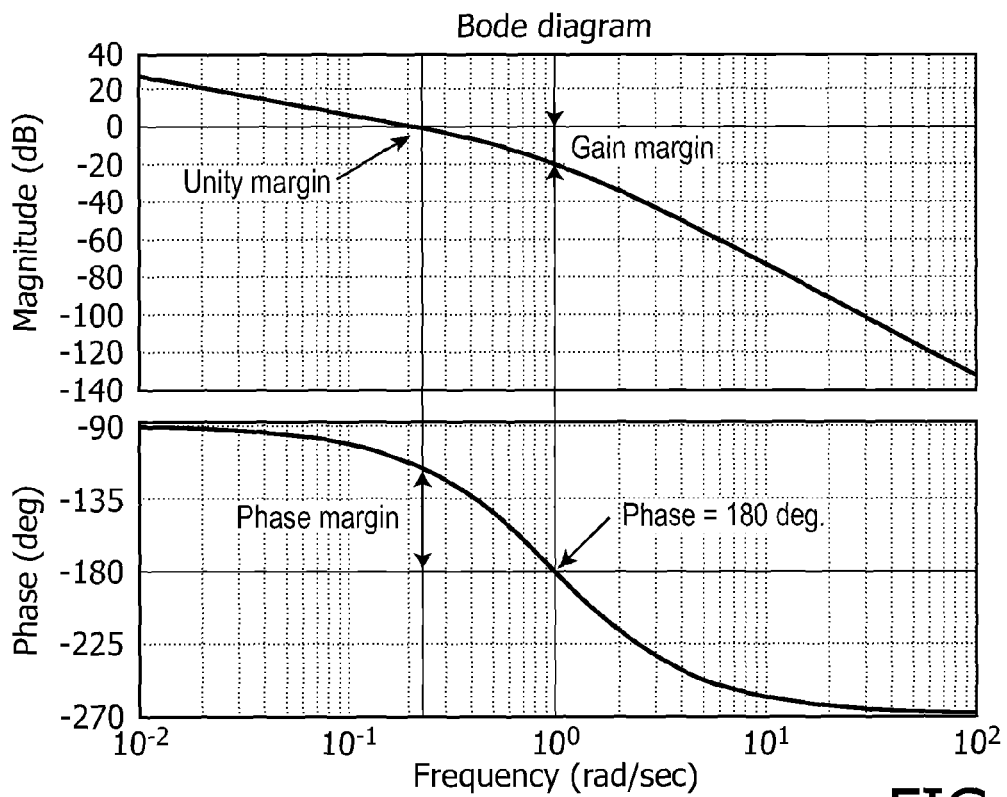
FIGS. 7-10 are Bode plot illustrating various aspects of closed loop control.

A Bode plot is a plot of the magnitude and phase of a transfer function versus frequency. The gain and phase margin of a system are two means of assessing system stability. The gain margin is the ratio between unity gain and the magnitude of the open-loop transfer function of a stable closed-loop system at the point in which the phase becomes less than −180°. When a 180° phase shift occurs, a sign inversion occurs causing negative feedback of the system to become positive feedback, which results in an unstable system for any gain greater than one. The phase margin is the difference between the phase of the transfer function of a stable closed-loop system and −180° at the point in which the gain of the system becomes less than unity. The Bode plot of the open loop system from FIG. 6 with a gain K=0.25 is shown in FIG. 7. The gain and phase margin for this system are also shown in FIG. 7. The gain margin in this example is approximately 20 dB which indicates that increasing the gain of the open-loop system by more than a factor of 10 will result in an unstable system.

Figure 8:
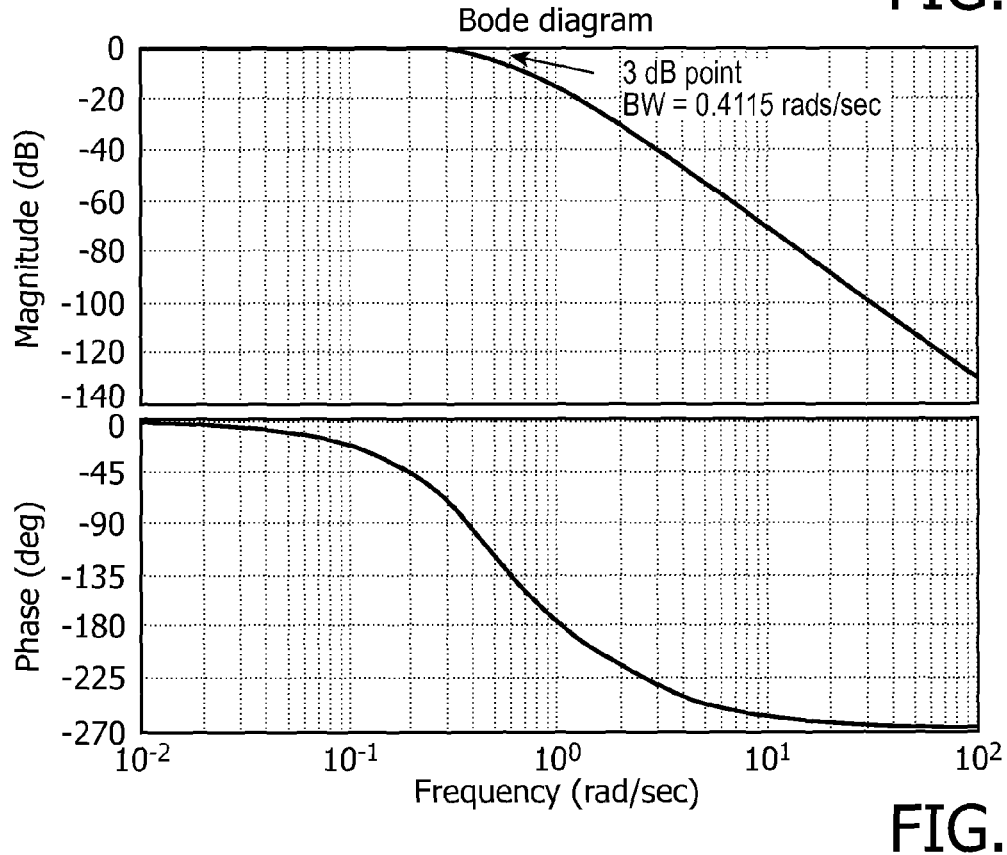

In addition to stability, the bandwidth of the closed-loop system is also an important design consideration. This is defined as the frequency at which the Bode plot is 3 dB less than the DC gain (or gain of the system at 0 Hz). The bandwidth of the system is a means of assessing response speed of the system to load-side disturbance changes and setpoint changes. There are other important design considerations in addition to stability and bandwidth; however, for the purposes of this discussion, only these two will be considered. The Bode plot and illustration of bandwidth of the closed-loop system with gain K=0.25 from FIG. 6 is shown in FIG. 8 (this is a Bode Plot of closed-loop system with open-loop transfer function $$\frac{0.25}{s(s+1)^2}.$$

The closed-loop transfer function is $$\frac{0.25}{s^2+2s^2+s+0.25}\bigg).$$

As shown in the figure, the bandwidth of the system is 0.4115 rads/sec.

Figure 9:
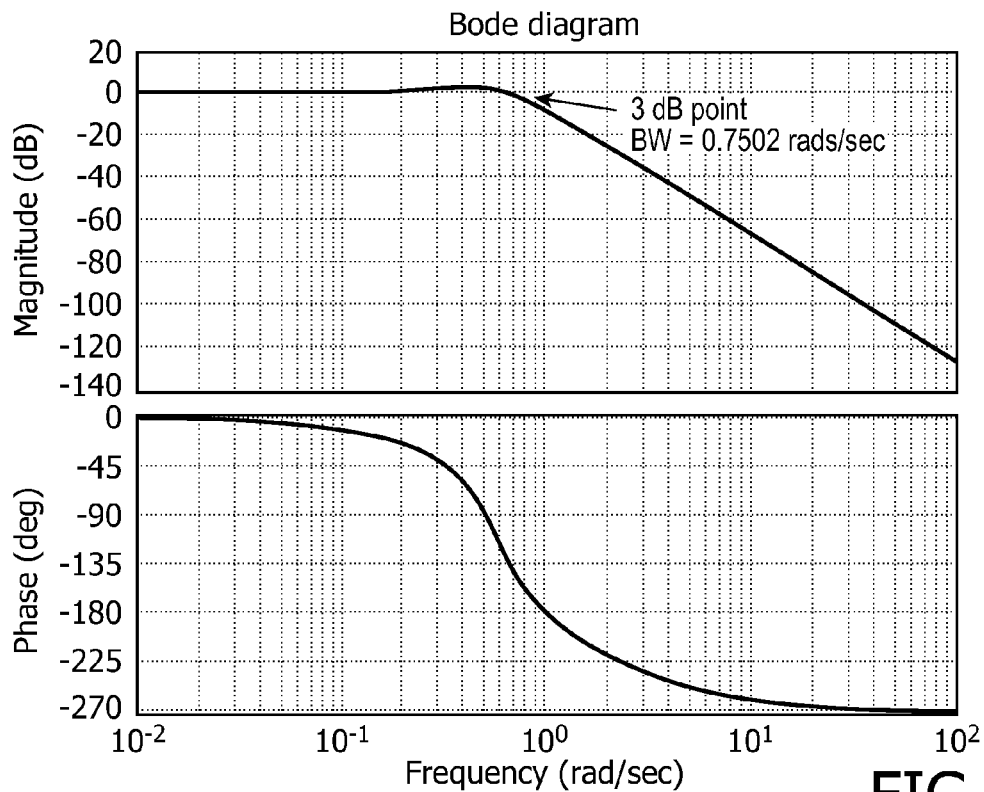

If the gain of the system is doubled, this will remain stable since this is less than the gain margin of 20 db (or factor of 10) previously mentioned. The Bode plot for the closed-loop system with K=0.5 is shown in FIG. 9 (this is a Bode plot of the closed-loop system with open-loop transfer function $$\frac{0.5}{s(s+1)^2}$$

(K=0.5); this represents a gain of 2 over the previous system; the close-loop transfer function is $$\frac{0.5}{s^2+2s^2+s+0.5};$$

note the bandwidth increase from the previous system). As shown in the figure, doubling the gain from K=0.25 to K=0.5 increased the bandwidth of the system from 0.4115 rads/sec to 0.7502 rads/sec, respectively. This yields better system response times than the system with a gain of K=0.25.

Figure 10:
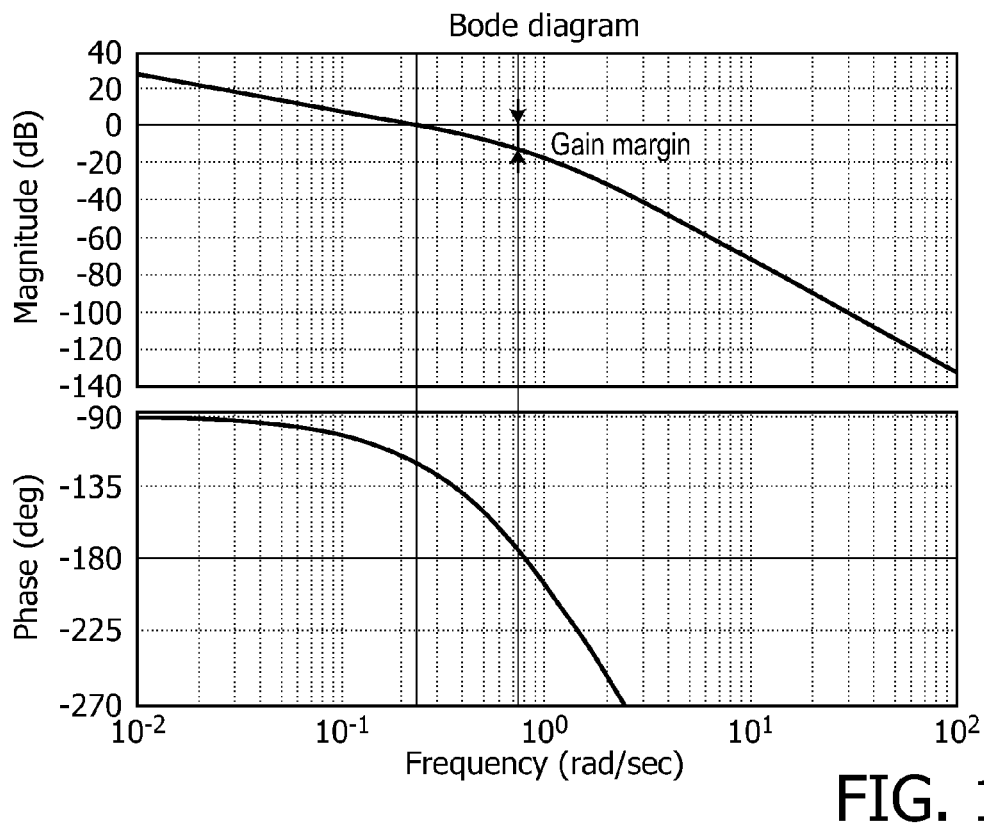

A pure time delay in a control system contributes a linearly increasing phase lag in which the degree of negative phase contribution is proportional to frequency. The slope of this line is proportional to the amount of time delay. A time delay of 0.3 seconds was added to the system from FIG. 8 with a gain of K=0.25. This delay affects only the phase of the system, thereby decreasing the gain margin as shown in FIG. 10 (Bode plot of a System with Open-Loop Transfer Function $$\frac{0.25}{s(s+1)^2}$$

Demonstrating Gain and Phase Margins (K=0.25)). If the increase in delay is large enough, this necessitates a decrease in gain to maintain stability or limit other undesirable effects, effectively limiting the response speed of the system. For a PAP application, this has effects on both the pressure setpoint response as well the load-side flow disturbance response.

Figure 11:
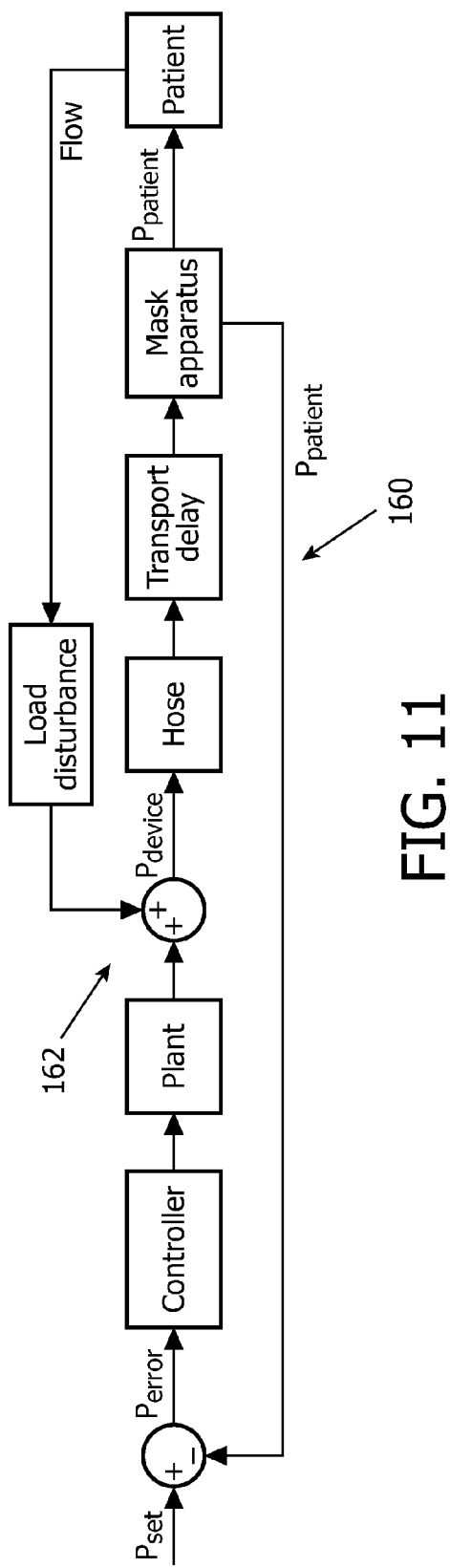
FIG. 11 is a block diagram of a closed-loop feedback system of the pressure loop of a PAP device with the pressure loop closed around patient pressure.

Because of this, for optimal pressure control at the patient, it is desirable to minimize time delays within the system. This necessitates placing the pressure sensor and pressure control mechanism as close to the patient as possible. Consider the case where only the pressure sensor is placed at the mask as shown in FIG. 11, which is a block diagram of a closed-loop feedback system 160 of the pressure loop of a PAP device 162 with the pressure loop closed around patient pressure. If the pressure loop is closed using feedback from the pressure sensor at the mask, the transport delay as a result of the hose becomes a part of the closed-loop system. As shown previously, this has negative effects on system response.

Figure 12:
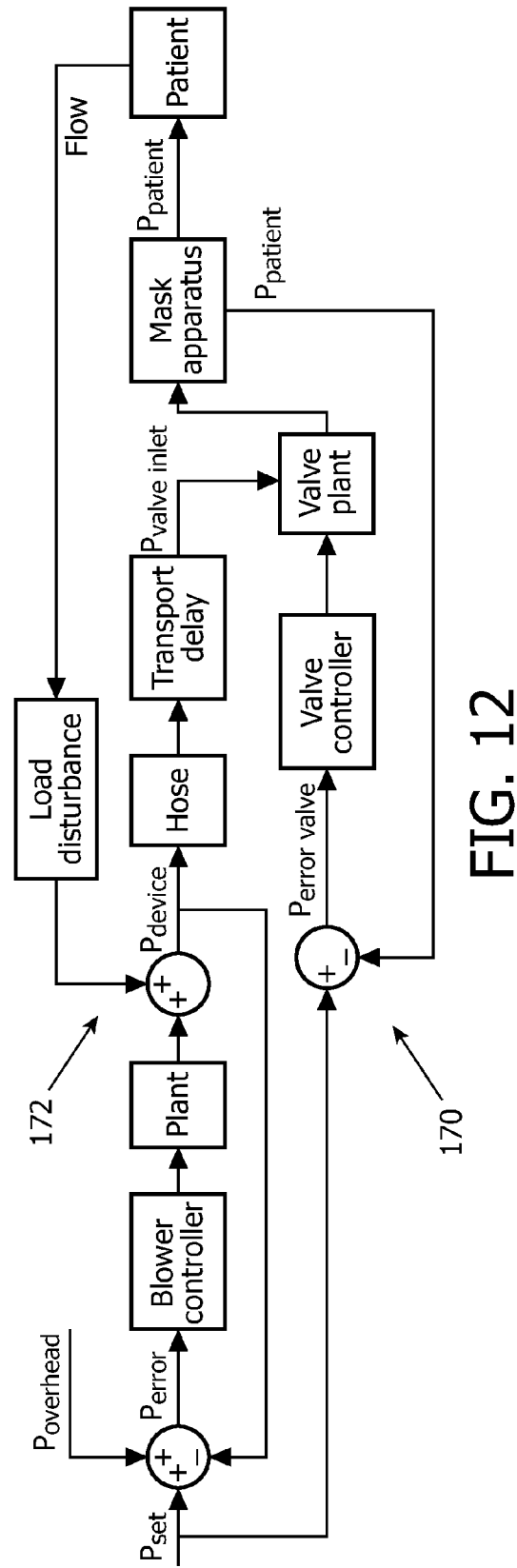
FIG. 12 is a block diagram of a closed-loop feedback system of a PAP device which includes a separate control loop for the valve which is not affected directly by transport delay

However, if the blower control loop is used to provide a pressure that is greater than the pressure to be delivered to the patient, this can provide a bias pressure to the valve. The valve and a separate control loop can be used to control the pressure delivered to the patient. FIG. 12 is a block diagram of a closed-loop feedback system 170 of PAP device 172 which includes a separate control loop for the valve which is not affected directly by transport delay. In this configuration the transport delay does not affect either control loop thereby improving system response.

Additionally, system response dynamics are in some manner limited by the response time of the pressure generation device. In the exemplary, non-limiting case of a centrifugal pump, the mass moment of inertia of the impeller is a critical system-level component which affects the pressure slew-rate (the change in pressure per unit time.) The device that provides the torque (again, in this particular case the motor) must overcome this term to accelerate or decelerate the pump to achieve a rapid change in speed and therefore, outlet pressure as seen in the following system torque relationship:

$$\tau_{sm} = j\frac{d\omega}{dt} + \tau_{airload} + \tau_{windage} + \tau_{friction} + \tau_{residual}.$$

This gives rise to the mechanical response time of the pump. Conversely, the response time of a valve is determined in part by the mass of the mobile valve component and is seen in the following system force relationship:

$$F = m\frac{dv}{dt} + F_{friction} + F_{residual}.$$

The outlet pressure of a centrifugal pump is a function of speed and change in radius the fluid encounters in the impeller. Largely, a smaller impeller must be run at a higher speed to achieve the same pressure as a larger impeller; however, this tends to increase the mass moment of inertia of the system (proportional to $mr^2$) requiring more torque to accelerate (change the pressure) in the blower. Multistage pump approaches increase the mass moment of inertia as well.

Considering the typical diameter of the centrifugal pump impeller required to provide therapy and the mass of the mobile valve component it is therefore possible to provide much faster pressure slew-rates with a valve in combination with some biasing pressure than with a centrifugal pump alone.

Figure 13:
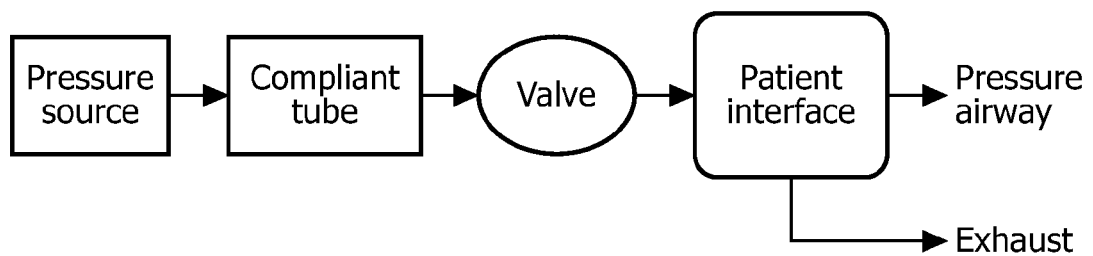
FIG. 13 is a block diagram of the pressure support system according to a first embodiment of the present invention.
Figure 14:
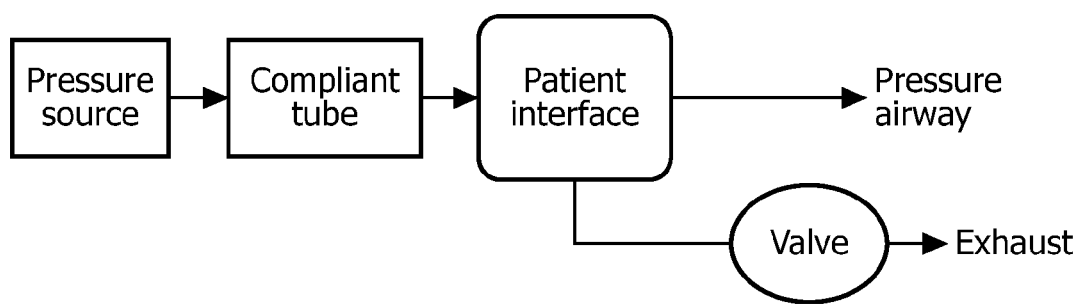
FIG. 14 is a is a block diagram of the pressure support system according to a second embodiment of the present invention.

In the embodiment described above, the valve is disposed downstream of the pressure source and upstream of the patient interface that is in communication with the airway of the user. See FIG. 13. The present invention also contemplates locating the valve at other locations so long as it provides the function of control the flow and/or pressure of gas at the patient interface. For example, FIG. 14 shows an example in which the valve is provided to control the flow of exhaust gas exiting the patient interface (i.e., mask). In addition, a pressure sensor is integrated into or otherwise configured to measure the pressure in the patient interface (e.g. a mask). The pressure sensor and valve are connected to a common controller module that adjusts the position of the valve based on input from the pressure sensor.

By placing a pressure sensor in the patient interface, changes in patient condition (inhalation, exhalation, apnea, etc) can be detected much more quickly than in a traditional arrangement wherein sensors are typically located only in the pressure source (due to the length of the connection tube). Additionally, by placing a controlled variable resistance valve downstream from the mask and in the exhaust gas flow, air flow from the pressure source can be diverted to/from the exhaust in order to adjust the portion of the air flow directed into the patient's airway. Because the valve is placed proximal to the patient interface, these air flow adjustments can be made more quickly than adjustments made by the pressure source controller. The combination of quick pressure measurements and flow adjustments would allow the device to better react to changes in patient condition and potentially improve the efficacy of the device as well as patient comfort.

In one embodiment this invention is used as part of a system to provide CPAP therapy. A mask which seals to the patient's face and covers the patient's nose, and optionally, mouth is used as the patient interface. The pressure sensor is mounted at the inlet of the mask (downstream from the connection tube) such that it is in fluid connection with the mask chamber. The pressure sensor is also connected via a series of wires to a controller module which is integrated into the pressure source. The actively controlled valve consists of a motorized ball valve and is mounted between the mask chamber and the atmosphere in order to function as an exhaust when in a partially or fully open position. The ball valve is designed such that as the inner ball rotates from a closed to open position the resistance of the valve progressively decreases. The valve is connected via a series of wires to the controller module.

The present invention further contemplates that the controller module may be integrated into the patient interface or provided as a standalone module. In addition, the pressure sensor may be:
(1) mounted within the mask chamber,
(2) provided at a location external to the mask with a small tube providing a fluid connection to the chamber through the mask wall.
(3) external to the mask and not in direct fluid contact with the mask chamber, but mounted on a flexible portion of the mask wall with mechanical properties sufficient to allow the pressure within the mask to be accurately measured by the displacement of the wall membrane, and/or
(4) connected wirelessly to the controller module
The valve may be:
(1) comprised of any number of different variable resistance valve types
(2) mounted in line with a single mask exhaust or provide a parallel flow path to another existing exhaust of fixed resistance
(3) designed to fail "open" to provide a safety function in the case of device failure, and/or
(4) connected wirelessly to the controller module In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface assembly structured to be in fluid communication with a pressure source that provides a flow of a fluid, comprising:
    a patient interface device having a chamber formed therein that is structured to be in fluid communication with a breathing passage of a patient, the patient interface device being structured to be positioned on a head of the patient when the patient interface assembly is donned by the patient;
    a first pressure sensor structured to detect pressure conditions within the chamber, the first pressure sensor being structured to be positioned on the head of the patient when the patient interface assembly is donned by the patient;
    a valve adapted to adjust a pressure within the patient interface device when the patient interface assembly is donned by the patient, the valve being structured to be positioned on the head of the patient when the patient interface assembly is donned by the patient; and
    a compliant tube element having variable compliance and resistance properties and being structured to be positioned on the head of the patient when the patient interface assembly is donned by the patient such that the compliant tube element extends for a length along the head of the patient, the patient interface device being positioned downstream of the valve through the tube element such the patient interface device is separated from the valve by the length of the compliant tube element that extends along the head of the patient, wherein closed loop control is employed to control the valve and thereby the pressure delivered to the patient through the patient interface device based on at least the pressure conditions detected by the first pressure sensor, and wherein the valve is structured to be positioned a certain distance from the breathing passage of the patient when the patient interface assembly is donned by the patient such that changes in the pressure delivered to the patient that result from action of the valve are communicated to the patient with a delay of under one millisecond, wherein the pressure source is upstream of the valve and separated from the head of the patient when the patient interface assembly is donned.

2. The patient interface assembly of claim 1, wherein the valve is structured to be positioned a distance of one foot or less from the breathing passage of the patient when the patient interface assembly is donned by the patient.

3. The patient interface assembly of claim 1, wherein first pressure sensor is positioned within the chamber.

4. The patient interface assembly of claim 1, further comprising a fluid connection apparatus in fluid communication with the patient interface device through the tube element and structured to receive the flow of fluid, the fluid connection apparatus having a housing coupled to the tube element and being structured to be positioned on the head of the patient when the patient interface assembly is donned by the patient, the first pressure sensor being disposed on or in the patient interface device and the valve being disposed on or in the housing.

5. The patient interface assembly of claim 4, wherein the first pressure sensor and the valve are part of a flow control circuit, wherein the flow control circuit further comprises a controller structured to receive an input signal from the first pressure sensor and being further structured to employ the closed loop control responsive at least in part to the input signal to provide to the valve an output signal for controlling the valve.

6. The patient interface assembly of claim 5, wherein at least a portion of the controller is disposed on or in at least one of the patient interface device and the housing.

7. The patient interface assembly of claim 6, wherein the housing comprises a manifold apparatus structured to receive the flow of fluid and wherein the tube element comprises at least a pair of fluid connection elements extending in fluid communication between the manifold apparatus and the patient interface device.

8. The patient interface assembly of claim 5, wherein the flow control circuit further comprises a wireless communication apparatus, the controller being structured to receive an input signal from the first pressure sensor and to provide an output signal to the valve, the wireless communication apparatus being structured to enable wireless transmission of at least one of the input signal and the output signal.

9. The patient interface assembly of claim 5, wherein the flow control circuit further comprises a second pressure sensor situated at an opposite side of the valve from the first pressure sensor.

10. The patient interface assembly of claim 9, wherein the first pressure sensor is disposed on or in the patient interface device, and wherein the second pressure sensor is disposed on or in the housing.

11. The patient interface assembly of claim 5, wherein at least one of the patient interface device, the fluid connection apparatus, and the flow control circuit comprises an exhaust port structured to be in fluid communication with the breathing passage of the patient, the first pressure sensor being structured to be situated between the exhaust port and the patient.

12. A method of providing a flow breathing gas to a patient, comprising:

positioning a patient interface assembly on a head of the patient, the patient interface assembly being in fluid communication with a pressure source that provides a flow of gas and including:
(i) a patient interface device having a chamber formed therein that is structured to be in fluid communication with a breathing passage of the patient, the patient interface device being structured to be positioned on a head of the patient when the patient interface assembly is donned by the patient;
(ii) a first pressure sensor structured to detect pressure conditions within the chamber, the first pressure sensor being structured to be positioned on the head of the patient when the patient interface assembly is donned by the patient;
(iii) a valve adapted to adjust a pressure within the patient interface device when the patient interface assembly is donned by the patient, the valve being structured to be positioned on the head of the patient when the patient interface assembly is donned by the patient; and
(iv) a compliant tube element having variable compliance and resistance properties and being structured to be positioned on the head of the patient when the patient interface assembly is donned by the patient such that the compliant tube element extends for a length along the head of the patient, the patient interface device being positioned downstream of the valve through the tube element such the patient interface device is separated from the valve by the length of the compliant tube element that extends along the head of the patient,
wherein the valve is adapted to control a pressure or flow of gas in the compliant tube;
detecting pressure conditions within chamber using the first pressure sensor; and
employing closed loop control to control the valve and thereby the pressure delivered to the patient through the patient interface device based on at least the pressure conditions detected by the first pressure sensor, wherein the valve is structured to be positioned a certain distance from the breathing passage of the patient when the patient interface assembly is donned by the patient such that changes in the pressure delivered to the patient that result from action of the valve are communicated to the patient with a delay of under one millisecond,
wherein the pressure source is upstream of the valve and separated from the head of the patient when the patient interface assembly is donned.

13. The method of claim 12, wherein the valve is structured to be positioned a distance of one foot or less from the breathing passage of the patient when the patient interface assembly is donned by the patient.

14. The method of claim 12, wherein patient interface assembly includes a fluid connection apparatus in fluid communication with the patient interface device through the tube element, the fluid connection apparatus having a housing coupled to the tube element and being structured to be positioned on the head of the patient when the patient interface assembly is donned by the patient, the first pressure sensor being disposed on or in the patient interface device and the valve being disposed on or in the housing.

* * * * *